(12) United States Patent
Neilan et al.

(10) Patent No.: US 8,927,217 B2
(45) Date of Patent: Jan. 6, 2015

(54) DETECTION OF HEPATOTOXIC CYANOBACTERIA

(75) Inventors: Brett A. Neilan, Maroubra (AU); Anne-Dorothee Jungblut, Quebec (CA)

(73) Assignee: NewSouth Innovations Pty Limited, New South Wales (AU)

( * ) Notice: Subject to any disclaimer, the term of this patent is extended or adjusted under 35 U.S.C. 154(b) by 1216 days.

(21) Appl. No.: 11/922,161

(22) PCT Filed: May 31, 2006

(86) PCT No.: PCT/AU2006/000730
§ 371 (c)(1),
(2), (4) Date: Sep. 8, 2008

(87) PCT Pub. No.: WO2006/128230
PCT Pub. Date: Dec. 7, 2006

(65) Prior Publication Data
US 2009/0275018 A1 Nov. 5, 2009

(30) Foreign Application Priority Data

May 31, 2005 (AU) .................. 2005902805

(51) Int. Cl.
*C12Q 1/68* (2006.01)
*C12Q 1/04* (2006.01)
*C12Q 1/52* (2006.01)
*C07H 21/04* (2006.01)

(52) U.S. Cl.
CPC .. *C12Q 1/04* (2013.01); *C12Q 1/52* (2013.01); *C12Q 1/689* (2013.01)
USPC ...................... 435/6.12; 536/24.33

(58) Field of Classification Search
None
See application file for complete search history.

(56) References Cited

FOREIGN PATENT DOCUMENTS

WO    WO 2004/104211 A2    12/2004

OTHER PUBLICATIONS

Vaitomaa et al. Applied and Environmental Microbiology vol. 69:7289-7297. 2003.*
Lowe et al. Nucleic Acids Research vol. 18:1757-1762. 1991.*
Surakka et al. Benthic cyanobacteria from the Baltic Sea contain cytotoxic Anabaena, Nodularia, and Nostoc strains and an apoptosis-inducing Phormidium strain. Environmental Toxicology 20(3):285-292, first published online May 12, 2005.*
GenBank AY210783 [online] Jan. 25, 2005 [retrieved on Aug. 28, 2013] retrieved from http://www.ncbi.nlm.nih.gov/nuccore/ay210783.*
GenBank AJ536156 [online] Apr. 15, 2005 [retrieved on Aug. 28, 2013] retrieved from http://www.ncbi.nlm.nih.gov/nuccore/aj536156.*
Lyra et al. Benthic cyanobacteria of the genus *Nodularia* are non-toxic, without gas vacuoles, able to glide and genetically more diverse than planktonic *Nodularia*. International Journal of Systematic and Evolutionary Microbiology 55:555-568 (2005).*
Beattie, Kenneth et al., "The cyanobacterium *Nodularia* PCC 7804, of freshwater origin, produces [L-Har²] nodularin"; Phytochemistry 54:57-61, 2000.

(Continued)

*Primary Examiner* — Samuel Woolwine
(74) *Attorney, Agent, or Firm* — Kilpatrick Townsend & Stockton LLP

(57) ABSTRACT

The present invention relates to methods and kits for the detection of toxic cyanobacteria, in particular of hepatotoxin-producing cyanobacteria.

6 Claims, 4 Drawing Sheets

| | | | | |
|---|---|---|---|---|
| HEPF | 5' | TTTGGGGTT AACTTTTTT GGCCATAGT C | 3' | |
| *N. spumigena* NSOR10 | | TTTGGGGTT AACTTTTTT GGTCATAGT C | -------- | AACCCGAT TTACAGCCT CAAGAATT |
| *Anabaena* sp. 90 | | TTTGGAGTT AACTTTTTT GGGCATAGT C | -------- | AACCAGAT TTACAGCCT AAAGAATT |
| *M. aeruginosa* PCC7806 | | TTTGGGGTT AACTTTTTT GGGCATAGT C | -------- | AACCCGAT TTACAGCCT CAAGAATT |
| *M. aeruginosa* K-139 | | TTTGGGGTT AACTTTTTT GGGCATAGT C | ------- | AACCCGAT TTACAGCCT CAAGAATT |
| *Planktothrix* sp. 126/8 | | TTTGGGGTT AACTTTTTT GGGCATAGT C | -------- | AACCCGAT TTACAACCT CAAGAATT |
| HEPR | | | 3' | AACCCGAT TTACAGCCT CAAGAATT 5' |
| Consensus | | ***G* ******* G****** * | | **C* ***G* C******* |

(56) References Cited

OTHER PUBLICATIONS

Bolch, Christopher J. S. et al., "Genetic, morphological, and toxicological variation among globally distributed strains of *Nodularia* (cyanobacteria)[1]"; J. Phycol. 35:339-355, 1999.
Burns, Brendan P. et al., "Molecular detection of genes responsible for cyanobacterial toxin production in the genera Microcystis, *Nodularia*, and Cylindrospermopsis"; Methods in Molecular Biology, 268:213-222, 2004.
Carmichael, Wayne W., "Chemical and toxicological studies of the toxic freshwater cyanobacteria *Microcystis aeroginosa, Anabaena flos-aquae* and *Aphanizomenon flos-aquae*"; South African Journal of Science 78:367-372, Sep. 1982.
Carmichael, Wayne W., "Health effects of toxin-producing cyanobacteria: 'The CyanoHABs'"; Human and ecological risk assessment 7:1393-1407, 2001.
Chorus, Ingrid and Bartram, Jamie, "Toxic cyanobacteria in water: a guide to their public health consequences, monitoring and management"; World Health Organisation, E & FN Spon, London,1999.
Christiansen, Guntram et al., "Microcystin biosynthesis in *Planktothrix*: genes, evolution, and manipulation"; Journal of Bacteriology 185(2):564-572, Jan. 2003.
Codd, Geoffrey A. et al., "Cyanobacterial toxins, exposure routes and human health"; Eur. J. Phycol. 34:405-415. 1999.
Doers, Mary P. and Parker, Dorothy L. "Properties of *Microcystis aeruginosa* and *M. flos-aquae* (Cyanophyta) in culture: taxonomic implications[1]"; J. Phycol. 24:502-508, 1988.
Eloff, J. N., and Van Der Westhuizen, A. J, "Toxicological studies on *Microcystis*"; W. W. Carmichael (ed.), The Water Environment—Algal Toxins and Health. Plenum. Press, New York, pp. 343-364, 1981.
Ernst, Bernhard et al., "Presence of *Planktothrix* sp. and cyanobacterial toxins in Lake Ammersee, Germany and their impact on whitefish (*Corregonus lavaretus* L.)"; Environ. Tox. 16:483-488, 2001.
Hawkins, Peter R. et al., "Isolation and toxicity of *Cylindrospermopsis raciborskii* from an ornamental lake"; Toxicon 35(3):341-346, 1997.
Hisbergues, Michael et al., "PCR-based identification of microcystin-producing genotypes of different cyanobacterial genera"; Arch. Microbiol. 180:402-410, 2003.
Hitzfeld, Bettina C. et al., "Cyanobacterial toxins: removal during drinking water treatment, and risk assessment"; Environ. Health Perspectives 108(1):113-122, 2000.
Jungblut, Anne-Dorothee et al., "Molecular identification and evolution of the cyclic peptide hepatotoxins, microcystin and nodularin, synthetase genes in three orders of cyanobacteria"; Archives of Microbiology (2006) 185:107-114, Jan. 10, 2006, Springer-Verlag.
Kaebernick, Melanie et al., "Ecological and molecular investigations of cyanotoxin production"; FEMS Microbiology Ecology 351:1-9, 2001.
Kurmayer, Rainer and Krutzenberger, T. "Application of real-time PCR for quantification of microcystin genotypes in a population of the toxic cyanobacterium *Microcystis* sp"; Applied and Environmental Microbiology, 69(11):6723-6730, Nov. 2003.
Kurmayer, Rainer et al., "Abundance of active and inactive microcystin genotypes in populations of the toxic cyanobacterium *Planktothrix* spp"; Environ. Microbiol. 6(8):831-841, 2004.
Lehtimäki, J. et al., "The effects of incubation time, temperature, light, salinity, and phosphorus on growth and hepatotoxin production by Nodularia strains"; Arch. Hydrobiol. 130(3):269- 282, May 1994.
Lyra, Christina et al., "Molecular characterization of planktic cyanobacteria of *Anabaena, Aphanizomenon, Microcystis* and *Planktothrix* genera"; Int. J. Syst. Evol. Microbiol. 51:513-526, 2001.
Mikalsen, Bjorg et al., "Natural variation in the microcystin synthetase operon mcyABC and impact on microcystin production in Microcystis strains"; J. Bacteriol. 185(9):2774-2785, May 2003.
Moffitt, Michelle C. and Neilan, Brett A., "Characterization of the nodularin synthetase gene cluster and proposed theory of the evolution of cyanobacterial hepatotoxins"; Appl. Environ. Microbiol. 70(11):6353-6362, Nov. 2004.
Moffitt, Michelle C. and Neilan, Brett A., "On the presence of peptide synthetase and polyketide synthetase genes in the cyanobacterial genus *Nodularia*"; FEMS Microbiol. Lett. 196:207-214, 2001.
Neilan, Brett A., "Detection and identification of cyanobacteria associated with toxic blooms: DNA amplification protocols"; Phycologia 35(6):147-155, 1996.
Neilan, Brett A., "Identification and phylogenetic analysis of toxigenic cyanobacteria by multiplex randomly amplified polymorphic DNA PCR"; Appl. Environ. Microbiol. 61(6):2286-2291, 1995.
Neilan, Brett A., et al., "Molecular identification of cyanobacteria associated with stromatolites from distinct geographical locations"; Astrobiol. 2(3):271-280, 2002.
Neilan, Brett A., et al., "Nonribosomal peptide synthesis and toxigenicity of cyanobacteria"; J. Bacteriol. 181(13):4089-97, Jul. 1999.
Nishizawa, Tomoyasu et al., "Genetic analysis of the peptide synthetase genes for a cyclic heptapeptide microcystin in *Microcystis* spp"; J. Biochem. 126:520-529, 1999.
Ouahid, Youness et al., "Identification of potentially toxic environmental *Microcystis* by individual and multiple PCR amplification of specific microcystin synthetase gene regions"; Environmental Toxicology, 20(3):235-242, 2005.
Pearson Leanne A. et al., "The molecular genetics of cyanobacterial toxicity as a basis for monitoring water quality and public health risk"; Current Opinion in Biotechnology, London, GB; 19(3):281-288, 2008.
Prinsep, Michele R., et al., "Microcystin-LA from a blue-green alga belonging to the Stignonematales"; Phytochemistry 31(4):1247-1248, 1992.
Rantala, Anne et al., "Phylogenetic evidence for the early evolution of the microcystin synthesis"; PNAS 101(2):568-573, Jan. 13, 2004.
Rouhiainen, Leo et al., "Genes coding for hepatotoxic heptapeptides (microcystins) in the cyanobacterium *Anabaena* strain 90"; Appl. Environ. Microbiol. 70(2):686-692, Feb. 2004.
Sivonen, Kaarina and Jones, Gary, "Toxic cyanobacteria in water: a guide to their public health consequences, monitoring and management"; Cyanobacterial Toxins, Chapter 3, p. 41-111, In I Chorus and J. Bartram (ed.), World Health Organisation; E&FN Spon. London, 1999.
Sivonen, Kaarina et al., "Three new microcystins, cyclic heptapeptide hepatotoxins, from *Nostoc* sp. strain 152"; Chem. Res. Toxicol. 5:464-469, 1992.
Sivonen, Kaarina, "Effects of light, temperature, nitrate, orthophosphate, and bacteria on growth of and hepatotoxin production by *Oscillatoria agardhii* strains"; Appl. Environ Microbiol. 56(9):2658-2666, Sep. 1990.
Starr, Richard C. and Zeikus, Jeffrey A. "UTEX-The culture collection of algae at the University of Texas at Austin 1993 list of cultures"; J. Phycol. 29 (Suppl.):1-106, 1993.
Thompson, Julie D. et al., "Clustal W; improving the sensitivity of progressive multiple sequence alignment through sequence weighting, position-specific gap penalties and weight matrix choice"; Nucleic Acids Res. 22(22):4673-4680, 1994.
Tillet, Daniel et al. "Detection of toxigenicity by a probe for the microsystin synthetase A gene (*mcyA*) of the cyanobacterial genus *Microsystis*: Comparison of toxicities with 16S rRNA and phycocyanin operon (phycocyanin intergenic spacer) phylogenies"; App. Environ. Microbiol. 67(6):2810-2818, Jun. 2001.
Tillet, Daniel et al. "Structural organization of microcystin biosynthesis in *Microcystis aeruginosa* PCC7806: an integrated peptide-polyketide synthetase system"; Chem. Biol. 7(10):753-764, 2000.
Vaitomaa, Jaana et al., "Quantitative real-time PCR for determination of microcystin synthetase E copy numbers for *Microcystis* and *Anabaena* in lakes"; Appl. Environ. Microbiol. 69(12):7289-7297, 2003.
Namikoshi et al., "Two New L-Serine Variants of Microcystins-LR and -RR from *Anabaena* sp. Strains 202 A1 and 202 A2", Toxicon 30(11):1457-1464, 1992.
Namikoshi et al., "Seven New Microcystins Possessing Two L-Glutamic Acid Units, Isolated from *Anabaena* sp. Strain 186", Chemical Research in Toxicology 11:143-149, 1998.

\* cited by examiner

HEPF 5' TTTGGGGTT AACTTTTTT GGCCATAGT C 3'

N. spumigena NSOR10    TTTGGGGTT AACTTTTTT GGTCATAGT C    ———    AACCCGAT TTACAGCCT CAAGAATT
Anabaena sp. 90        TTTGGAGTT AACTTTTTT GGGCATAGT C    ———    AACCAGAT TTACAGCCT AAAGAATT
M. aeruginosa PCC7806  TTTGGGGTT AACTTTTTT GGGCATAGT C    ———    AACCCGAT TTACAGCCT CAAGAATT
M. aeruginosa K-139    TTTGGGGTT AACTTTTTT GGGCATAGT C    ———    AACCCGAT TTACAGCCT CAAGAATT
Planktothrix sp. 126/8 TTTGGGGTT AACTTTTTT GGGCATAGT C    ———    AACCCGAT TTACAACCT CAAGAATT

HEPR 3' AACCCGAT TTACAGCCT CAAGAATT 5'

Consensus ****G* *********

DETECTION OF HEPATOTOXIC CYANOBACTERIA

TECHNICAL FIELD

The present invention relates to methods and kits for the detection of toxic cyanobacteria, in particular of hepatotoxin-producing cyanobacteria.

BACKGROUND OF THE INVENTION

Cyanobacteria, also known as blue-green algae, are photosynthetic bacteria widespread in marine and freshwater environments worldwide. Of particular significance for water quality and human and animal health are those cyanobacteria which produce toxic compounds. A diverse range of cyanobacterial genera are well known for the formation of toxic blue-green algal blooms on water surfaces (see, for example, Codd et al., 1999; Carmichael, 2001). Many of these blooms are harmful to humans and animals due to the production of hepatotoxins and neurotoxins by the bloom-forming organisms and the ability of blooms to flourish and expand in coastal waters, streams, lakes, and in drinking water and recreational reservoirs.

There is a need for rapid methods for the accurate detection of toxic cyanobacteria to enable an assessment of the potential health hazard of cyanobacterial blooms and to allow the implementation of effective water management strategies to minimize the effects of toxic bloom outbreaks.

Two hepatotoxins of particular concern are microcystin and nodularin. Both toxins are inhibitors of eukaryotic-type protein phosphatases 1 and 2A and in vertebrates toxicity is mediated via transport of the toxins into hepatocytes. Acute exposure to either toxin can lead to liver failure and death in animals, including humans. Further, subchronic exposure to microcystin and nodularin is associated with tumor promotion and, in the case of nodularin, tumor initiation (Hitzfeld et al., 2000).

Microcystin and nodularin are cyclic peptides synthesized non-ribosomally by large multi-enzyme complexes consisting of different modules including non-ribosomal peptide synthetases (NRPS) and polyketide synthases (PKS) (Tillett et al., 2000; Moffitt and Neilan, 2001). These modules catalyze the activation, modification, and condensation of specific amino acids. Microcystins form a large family of cyclic heptapeptides of the general formula cyclo-(D-alanine-X-D-MeAsp-Z-Adda-D-glutamate-Mdha), where D-MeAsp is D-β-erythro-methyl-aspartatic acid, Mdha is N-methyldehydroalanine, and X and Z are variable L-amino acids. Nodularin is a cyclic pentapeptide of general formula cyclo-(D-MeAsp-L-arginine-Adda-D-glutamate-Mdhb), where Mdhb is 2-(methylamino)-2-dehydrobutyric-acid. The most unusual moiety of microcystin and nodularin is Adda (3-amino-9-methoxy-2,3,8-trimethyl-10-phenyl-4,6-decadienioc acid).

Microcystin-producing species usually produce a cocktail of different microcystin variants, however only one type will be predominately synthesized (Mikalsen et al., 2001). Only a few variants of nodularin have been identified to date.

To date there have been reports of microcystin production by cyanobacterial species from the four orders Chroococcales, Nostocales, Oscillatoriales, and Stignonematales, including *Microcystis* sp., *Chroococcus dispersus* (Chroococcales), *Anabaena* sp., *Nostoc* sp., *Anabeanopsis* sp. (Nostocales), *Haphalosiphon, Phormidium* sp., *Planktothrix* sp., and *Oscillatoria* sp. However, the genes for the production of nodularin have only been reported in *N. spumigena* and one *N. harveyana* strain (Moffitt and Neilan, 2001).

Due to this broad distribution of hepatotoxin production and sequence differences in cyanobacterial genera there is a lack of reliable molecular protocols that enable detection of all potentially hepatotoxin-producing cyanobacterial species. Most PCR-based detection methods are only based on the amplification of either microcystin or nodularin synthetase gene sequences from one genus or one species (for example Neilan, 1996; Moffitt et al., 2001; Tillet et al., 2000; Christiansen et al., 2003; Vaitomaa et al., 2003; Kurmayer et al., 2003, 2004). Protocols based on more than one data set only target the most common microcystin producing bloom-forming species *Microcystis, Planktothrix*, and *Anabaena* (Hisbergues et al., 2003). The molecular detection of other microcystin producing species such as *Anabaenopsis, Phormidium*, and *Nostoc* has not previously been addressed.

Accordingly, there is a clear need for the development of a simple detection system for the identification of multiple hepatotoxin-producing cyanobacterial species and genera.

The present inventors have now developed a molecular method that enables the detection of all known potentially microcystin and nodularin producing species with one single PCR reaction.

SUMMARY OF THE INVENTION

According to a first aspect of the present invention there is provided a method for the detection of toxic cyanobacteria, the method comprising the steps of:
(a) obtaining a cyanobacterial sample; and
(b) analyzing the sample for the presence of hepatotoxin-associated aminotransferase domain sequences,
wherein the presence of hepatotoxin-associated aminotransferase domain sequences are indicative of toxic cyanobacteria.

The hepatotoxin-associated aminotransferase domain sequences may be derived from the mcyE open reading frame of the microcystin synthetase gene complex or an orthologue or homologue thereof and/or the ndaF open reading frame of the nodularin synthetase gene complex or an orthologue or homologue thereof.

The analysis step (b) may comprise:
(i) amplification of DNA from the sample using suitable primers; and
(ii) detection of amplified sequences.

The primers may be oligonucleotide primers comprising the nucleotide sequences as set forth in any of SEQ ID Nos: 1 to 4. In one embodiment, the amplification may be performed using the primer pair comprising the nucleotide sequences as set forth in SEQ ID Nos: 1 and 2. In one embodiment, the amplification may be performed using the primer pair comprising the nucleotide sequences as set forth in SEQ ID Nos: 1 and 4. In one embodiment, the amplification may be performed using the primer pair comprising the nucleotide sequences as set forth in SEQ ID Nos: 3 and 4.

Detection of the amplified sequences may comprise gel electrophoresis and/or nucleic acid sequencing.

The cyanobacterial sample may comprise one or more isolated or cultured cyanobacterial organisms or may be an environmental sample containing one or more cyanobacterial organisms. The environmental sample may be a water sample or a sample from a blue-green algal bloom.

According to a second aspect of the present invention there is provided a method for the detection of hepatotoxin-producing cyanobacteria, the method comprising the steps of:

(a) obtaining a cyanobacterial sample; and
(b) analyzing the sample for the presence of hepatotoxin-associated aminotransferase domain sequences,
wherein the presence of hepatotoxin-associated aminotransferase domain sequences are indicative of hepatoxin-producing cyanobacteria.

The hepatotoxin may be microcystin or nodularin.

The hepatotoxin-associated aminotransferase domain sequences may be derived from the mcyE open reading frame of the microcystin synthetase gene complex or an orthologue or homologue thereof and/or the ndaF open reading frame of the nodularin synthetase gene complex or an orthologue or homologue thereof.

The analysis step (b) may comprise:
(i) amplification of DNA from the sample using suitable primers; and
(ii) detection of amplified sequences.

The primers may be oligonucleotide primers comprising the nucleotide sequences as set forth in any of SEQ ID Nos: 1 to 4. In one embodiment, the amplification may be performed using the primer pair comprising the nucleotide sequences as set forth in SEQ ID Nos: 1 and 2. In one embodiment, the amplification may be performed using the primer pair comprising the nucleotide sequences as set forth in SEQ ID Nos: 1 and 4. In one embodiment, the amplification may be performed using the primer pair comprising the nucleotide sequences as set forth in SEQ ID Nos: 3 and 4.

Detection of the amplified sequences may comprise gel electrophoresis and/or nucleic acid sequencing.

The cyanobacterial sample may comprise one or more isolated or cultured cyanobacterial organisms or may be an environmental sample containing one or more cyanobacterial organisms. The environmental sample may be a water sample or a sample from a blue-green algal bloom.

According to a third aspect of the present invention there is provided a kit for the detection of toxic cyanobacteria, the kit comprising at least one primer designed to detect hepatotoxin-associated aminotransferase domain sequences.

The kit may comprise multiple primers designed to amplify the hepatotoxin-associated aminotransferase domain sequences. The primers may be oligonucleotide primers comprising the nucleotide sequences as set forth in SEQ ID Nos: 1 to 4. The oligonucleotide primers may comprise the nucleotide sequences as set forth in SEQ ID Nos: 1 and 2. The oligonucleotide primers may comprise the nucleotide sequences as set forth in SEQ ID Nos: 1 and 4. The oligonucleotide primers may comprise the nucleotide sequences as set forth in SEQ ID Nos: 3 and 4.

According to a fourth aspect of the present invention there is provided a kit for the detection of hepatotoxin-producing cyanobacteria, the kit comprising at least one primer designed to detect hepatotoxin-associated aminotransferase domain sequences.

The kit may comprise multiple primers designed to amplify the hepatotoxin-associated aminotransferase domain sequences. The primers may be oligonucleotide primers comprising the nucleotide sequences as set forth in SEQ ID Nos: 1 to 4. The oligonucleotide primers may comprise the nucleotide sequences as set forth in SEQ ID Nos: 1 and 2. The oligonucleotide primers may comprise the nucleotide sequences as set forth in SEQ ID Nos: 1 and 4. The oligonucleotide primers may comprise the nucleotide sequences as set forth in SEQ ID Nos: 3 and 4.

Definitions

The term "hepatotoxin-associated aminotransferase domain sequence" as used herein means a nucleotide sequence encoding an aminotransferase activity that functions in the addition of an amino group to a cyclic peptide hepatotoxin. Typically the aminotransferase domain sequence is part of an open reading frame (ORF) encoding a multienzyme complex functioning in the production of the hepatotoxin, the ORF being physically located within the hepatotoxin biosynthetic gene cluster, as in the case of the mcyE ORF of the microcystin synthetase gene complex and the ndaF ORF of the nodularin synthetase gene complex. Alternatively the aminotransferase domain may be located within a separate gene encoding an aminotransferase enzyme.

In the context of this specification, the term "comprising" means "including principally, but not necessarily solely". Furthermore, variations of the word "comprising", such as "comprise" and "comprises", have correspondingly varied meanings.

BRIEF DESCRIPTION OF THE DRAWINGS

Embodiments of the present invention will now be described, by way of example only, with reference to the accompanying drawings.

FIG. 1. Alignment of the HEPF and HEPR primers with the aminotransferase target region from the characterized hepatotoxic species *Nodularia* NSOR10 (SEQ ID NO:5) (Moffitt and Neilan, 2004), *Anabaena* strain 90 (SEQ ID NO:6) (Rouhiainen et al., 2004), *M. aeruginosa* PCC7806 (SEQ ID NO:7) (Tillett et al., 2000), *M. aeruginosa* K-139 (SEQ ID NO:8) (Nishizawa et al., 1999), and *Planktothrix* NIVA-CYA126/8 (SEQ ID NO:9) (Christiansen et al, 2003).

Figure 2:
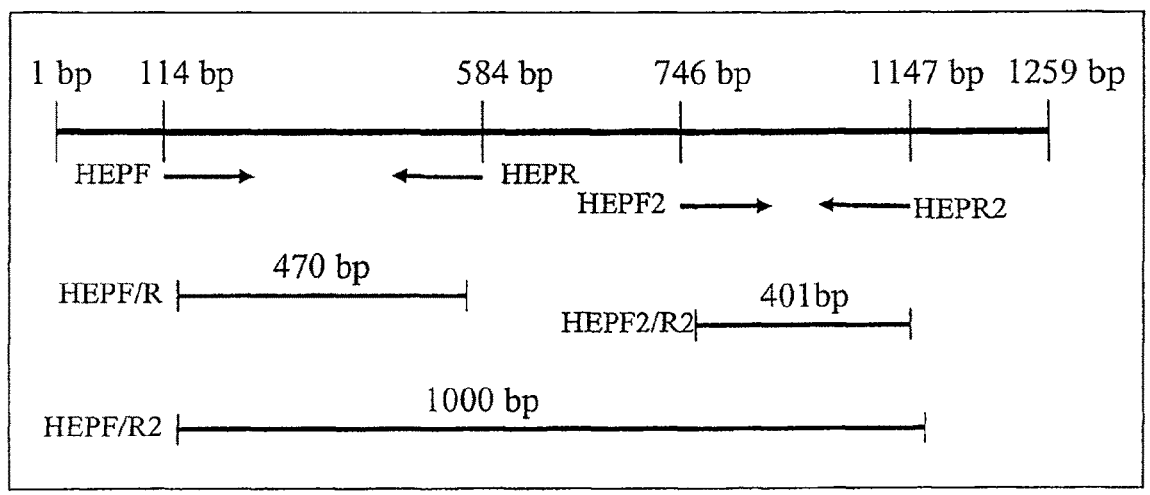
FIG. 2. Relative positions of primers HEPF, HEPR, HEPF2 and HEPR2 and approximate sizes (bp) of PCR products.

The nucleotide sequence of the oligonucleotide primer HEPF is set forth in SEQ ID No:1 and the nucleotide sequence of the oligonucleotide primer HEPR is set forth in SEQ ID No:2. The nucleotide sequence of the oligonucleotide primer HEPF2 is set forth in SEQ ID No:3. The nucleotide sequence of the oligonucleotide primer HEPR2 is set forth in SEQ ID No:4.

BEST MODE OF PERFORMING THE INVENTION

The invention will now be described in more detail, including, by way of illustration only, with respect to the examples which follow.

As described herein, the present inventors have developed a molecular tool enabling the successful identification of potentially hepatotoxic cyanobacterial species and blue-green algal blooms. The tool resides in a single PCR reaction based on the presence/absence of an aminotransferase (AMT) domain within the hepatotoxin synthesis gene cluster. The AMT domain is located between the polyketide synthase (PKS) and non-ribosomal peptide synthetase (NRPS) modules within the mcyE and ndaF open reading frames of the microcystin and nodularin synthetase enzyme complexes, respectively. AMT plays a critical role in the biosynthesis of microcystins and nodularins for the transfer of an amino group to the Adda moiety (Tillett et al., 2000).

Accordingly, one aspect of the present invention provides a method for the detection of toxic cyanobacteria, the method comprising the steps of:

(a) obtaining a cyanobacterial sample; and
(b) analyzing the sample for the presence of hepatotoxin-associated aminotransferase domain sequences, wherein the presence of hepatotoxin-associated aminotransferase domain sequences are indicative of toxic cyanobacteria.

The present invention also provides kits for the detection of toxic cyanobacteria the kits comprising at least one primer designed to detect hepatotoxin-associated aminotransferase domain sequences.

As exemplified herein, using the method according to an embodiment of the invention, hepatotoxic cyanobacteria cultures, as well as blue-green algal blooms, from the orders Oscillatoriales, Chroococcales and Nostocales were successfully detected. Furthermore, the genera of the identified hepatotoxic cyanobacteria could be determined by sequence analysis due to the congruence of species and peptide hepatotoxin evolution in cyanobacteria.

The methods and kits of the present invention provide a valuable tool for the detection of potentially toxic cyanobacterial isolates, for example, from water samples, thereby enabling the assessment of the potential for a toxic bloom to form, the identification of toxic blooms, or an assessment of the toxic potential, and thus the health hazard posed by, a blue-green algal bloom, Accordingly, the methods and kits of the invention may form part of routine water quality monitoring procedures or be used as required in the event of a blue-green algal bloom outbreak or in conditions considered likely to support or be conducive to such an outbreak.

Those skilled in the art will appreciate that the methods and kits of the present invention may be used alone or in conjunction with other available testing in identifying toxic cyanobacterial species and blooms.

It will be appreciated by those skilled in the art that the cyanobacteria to which the present invention relates are any potentially hepatotoxic cyanobacteria, typically being those capable of production of microcystin or nodularin. For example, the cyanobacteria to which the present invention is applicable may be selected from the orders Oscillatoriales, Chroococcales, Nostocales and Stigonematales. For example, the cyanobacteria may be selected from the genera *Anabaena, Nostoc, Microcystis, Planktothrix, Oscillatoria, Phormidium*, and *Nodularia*. For example, the cyanobacteria may be selected from the species *Microcystis aeruginosa, Microcystis viridis, Microcystis wesenbergii, Nodularia harveyana* and *Nodularia spumigena*. For example, the cyanobacteria may be selected from *Microcystis aeruginosa* PCC7806, *Microcystis aeruginosa* PCC7005, *Microcystis viridis* NIES 102, *Microcystis wesenbergii* NIES 107, *Microcystis* sp. strain UTEX 2667, *Microcystis* sp. strain UTEX 2664, *Nodularia harveyana* PCC7804, *Nodularia spumigena* NROS 10, *Nodularia spumigena* BY1, *Nodularia spumigena* HEM, *Anabaena* sp. strain 202A2, *Nostoc* sp. strain 152, *Oscillatoria* sp. strain 18R, *Oscillatoria* sp. strain 195, *Phormidium* sp. isolate 2-26b, *Phormidium* sp. isolate 1-6c and *Phormidium* sp. isolate 4-19b.

The methods and kits of the invention may also be employed for the discovery of novel hepatotoxic species or genera in culture collections or from environmental samples.

Methods and Kits

DNA to be analysed using methods and kits of the present invention may be extracted from cyanobacterial cells, either in mixed culture or as individual species or genus isolates. Accordingly, the cells may be cultured prior to DNA isolation or alternatively DNA may be extracted directly from environmental samples, such as water samples or blue-green algal blooms. A number of suitable methods known to those skilled in the art may be used for the extraction and purification of DNA for the purposes of the present invention, for example as described in Neilan (1995) and Neilan et al. (2002) the disclosures of which are incorporated herein by reference. Those skilled in the art will readily appreciate that the present invention is not to be limited to the use of specific methods for DNA isolation. Indeed the present invention may be performed without DNA isolation prior to DNA analysis.

Typically, according to methods of the invention the analysis of DNA is carried out by PCR amplification. Amplified products may be further analysed by nucleic acid sequencing. PCR amplification may be conducted on DNA extracted from cyanobacterial isolates or environmental samples as described above, or alternatively sequences may be amplified directly from organisms without the need for prior DNA extraction or purification steps. A variety of methods for direct PCR are known to those skilled in the art.

The methods and reagents for use in PCR amplification reactions, subsequent fragment resolution, and nucleic acid sequencing are well known to those skilled in the art. In each case, suitable protocols and reagents will largely depend on individual circumstances. Guidance may be obtained from a variety of sources, such as for example Sambrook et al., *Molecular Cloning: A Laboratory Manual*, Cold Spring Harbor, N.Y., 1989, and Ausubel et al., *Current Protocols in Molecular Biology*, Greene Publ. Assoc. and Wiley-Intersciences, 1992. A person skilled in the art would readily appreciate that various parameters of these procedures may be altered without affecting the ability to achieve the desired product. For example, in the case of PCR amplification, the salt concentration may be varied or the time and/or temperature of one or more of the denaturation, annealing and extension steps may be varied. Similarly, the amount of DNA used a template may also be varied depending on the amount of DNA available or the optimal amount of template required for efficient amplification.

The primers for use in the methods and kits of the present invention are typically oligonucleotides of, generally, 15 to 30 bases in length. Such primers can be prepared by any suitable method, including, for example, direct chemical synthesis or cloning and restriction of appropriate sequences. Not all bases in the primer need reflect the sequence of the template molecule to which the primer will hybridize, the primer need only contain sufficient complementary bases to enable the primer to hybridize to the template. A primer may also include mismatch bases at one or more positions, being bases that are not complementary to bases in the template, but rather are designed to incorporate changes into the DNA upon base extension or amplification. A primer may include additional bases, for example in the form of a restriction enzyme recognition sequence at the 5' end, to facilitate cloning of the amplified DNA.

As exemplified herein, suitable primers for the amplification of AMT domain-containing products for detection of potentially hepatotoxic cyanobacteria may comprise nucleotide sequences as set forth in SEQ ID Nos: 1 to 4. Suitable primer pairs for PCR amplification may comprise nucleotide sequences as set forth in SEQ ID No: 1 and SEQ ID No:2, SEQ ID No: 1 and SEQ ID No:4, or SEQ ID No: 3 and SEQ ID No:4. However those skilled in the art will appreciate that the present invention is not limited to the use of the specific primers exemplified, but alternative primer sequences may also be used, provided the primers are designed appropriately so as to enable the amplification of AMT sequences from hepatoxic cyanobacteria. For example, in alternative embodiments, the nucleotide sequence of a primer may share at least 85%, at least 90%, or at least 95%, 96%, 97%, 98% or 99% identity with the sequence as set forth in SEQ ID Nos:1 to 4. Those skilled in the art will appreciate that one or base substitutions, additions or deletions of the sequence(s) of these sequences may be made in generating a sequence of at least 85%, at least 90%, or at least 95%, 96%, 97%, 98% or 99% identity.

Further, the location of suitable primers for the amplification of AMT sequences may be determined by such factors as G+C content and the ability for a sequence to form unwanted secondary structures.

Suitable primer sequences can be determined by those skilled in the art using routine procedures without undue experimentation.

Suitable methods of analysis of the amplified DNA are well known to those skilled in the art, for example, gel electrophoresis which may or may not be preceded by restriction enzyme digestion, and nucleic acid sequencing. Gel electrophoresis may comprise agarose gel electrophoresis or polyacrylamide gel electrophoresis, techniques commonly used by those skilled in the art for separation of DNA fragments on the basis of size. The concentration of agarose or polyacrylamide in the gel in large part determines the resolution ability of the gel and the appropriate concentration of agarose or polyacrylamide will therefore depend on the size of the DNA fragments to be distinguished.

Kits for use in detecting toxic cyanobacteria are also provided by the present invention. Typically, kits according to the present invention are designed specifically with components to enable the detection of AMT domain sequences and thereby facilitate the identification of potentially toxic cyanobacteria.

Accordingly, kits of the present invention may include one or more oligonucleotide primers that specifically hybridize to AMT domain sequences of cyanobacteria and enabling the detection of hepatoxic cyanobacteria. In such kits, appropriate amounts of the primers may be provided in suitable containers. The oligonucleotide primers may be provided suspended in an aqueous solution or as a freeze-dried or lyophilized powder, for example.

The appropriate sequences of the primers may vary. In one embodiment a kit of the invention comprises a primer pair suitable for the PCR amplification of AMT sequences from cyanobacteria. The primer pair may comprise sequences as set forth in SEQ ID Nos: 1 and 2. The primer pair may comprise sequences as set forth in SEQ ID Nos: 1 and 4. The primer pair may comprise sequences as set forth in SEQ ID Nos: 3 and 4. The amount of each primer supplied in the kit can be any appropriate amount, depending on the nature of the application, and typically may be an amount sufficient to prime at least several amplification reactions. A person skilled in the art would readily appreciate the appropriate amount of each primer to use in a single amplification reaction.

A kit according to the present invention may also include a suitable control template molecule and/or control primers for use in a control reaction. The design of suitable control templates and primers and of control reactions are well known to those skilled in the art.

A kit according to the present invention may additionally include other components for performing amplification reactions including, for example, DNA sample preparation reagents, appropriate buffers (e.g. polymerase buffer), salts (e.g. magnesium chloride), polymerase enzyme, and deoxyribonucleotides (dNTPs). The kit may further include the necessary reagents for carrying out analysis of the amplified DNA, such as an appropriate restriction enzyme(s), reaction buffer(s) for restriction enzyme digestion, and reagents for use in separating digested fragments (e.g. agarose) and/or nucleic acid sequencing. Typically, a kit may also include containers for housing the various components and instructions for using the kit components to conduct amplification reactions according to the present invention.

The present invention will now be further described in greater detail by reference to the following specific examples, which should not be construed as in any way limiting the scope of the invention.

EXAMPLES

Example 1

PCR Detection of Cyclic Peptide Hepatotoxin Genes

Oligonucleotide primers were designed to be suitable for the amplification of the aminotransferase (AMT) domain encoded within the mcyE microcystin synthetase and ndaF nodularin synthetase multienzyme complexes. The primer design was based on the four complete microcystin synthetase sequence of *Microcystis aeruginosa* PCC7806, *Microcystis aeruginosa* K-139, *Anabaena* strain 90, and *Planktothrix* sp. 128/6, as well as the nodularin synthetase gene of *Nodularia spumigena* NSOR10 (see FIG. 1). From these five sequences two conserved sites were identified that enabled the design of specific primers, HEPF and HEPR, as shown in FIG. 1 and in SEQ ID Nos: 1 and 2 respectively. Alternate primers, designated HEPF2 and HEPR2 were also designed and synthesized, these primers being complementary to target sequences about 170 bp and 560 bp downstream of the target sequences for HEPR (see FIG. 2). As illustrated in FIG. 2, PCR amplification was performed using the HEPF/HEPR primer set, the HEPF/HEPR2 primer set and the HEPF2/HEPR2 primer set to determine their ability to screen for cyanobacterial peptide hepatotoxin producers.

The specificity of the primers was tested using hepatotoxic cyanobacterial species in culture as well as total bloom material.

17 hepatotoxic cultures were tested (Table 1), belonging to the genera *Microcystis, Anabaena, Nostoc, Planktothrix, Oscillatoria, Phormidium*, and *Nodularia*. The presence of microcystin or nodularin in the investigated strains was known from previous studies. 12 non-toxic cultures were tested, from the genera *Microcystis, Anabaena, Nostoc, Nodularia, Lyngbya, Phormidium, Synechocystis*, and *Cylindrospermopsis*. The dominant bloom-forming genera in these samples were *Microcystis, Planktothrix*, and *Nodularia*.

Bloom samples screened (Table 2) were collected from Lake Alexandria, John Oldman Park and the Swan River, Australia. The bloom sample from Lake Spino (Italy) was supplied by Milena Bruno (Department of Environmental Hygiene, National Health Institute, Italy). *Planktothrix* sp. bloom isolate (Lake Ammersee, Germany) and *Phormidium* sp. isolates were supplied by Daniel Dietrich (University of Konstanz, Germany), and George Izaguirre, (Water Quality Section, Metropolitan Water District of Southern California, USA), respectively. Other cyanobacterial strains were obtained from the School of Biotechnology and Biomolecular Culture collection, University of New South Wales, Australia (Table 1).

Total genomic DNA of strains and bloom material was extracted using XS buffer (Neilan et al., 2002). Approximately 200 mg of cyanobacterial cells was used for each extraction. The cells were combined with 600 μl XS extraction buffer (1% potassium-methylxanthogenate; 800 mM ammonium acetate; 20 mM EDTA; 1% SDS; 100 mM Tris-

TABLE 1

Cyanobacterial species tested for hepatotoxin production

| Species | Strain | Hepatotoxic[1] | Hepatotoxin | Other Cyanotoxins | Origin | Reference |
|---|---|---|---|---|---|---|
| Chroococcales | | | | | | |
| Microcystis aeruginosa | PCC7806 | + | microcystin | — | The Netherlands | Rippka and Herdman (1992) |
| Microcystis aeruginosa | PCC7005 | + | microcystin | — | Scotland | Rippka and Herdman (1992) |
| Microcystis sp. | UTEX 2667 | + | microcystin | — | United States | Eloff and van der Westhuizen (1981) |
| Microcystis sp. | UTEX 2664 | + | microcystin | — | United States | Eloff and van der Westhuizen (1981) |
| Microcystis viridis | NIES 102 | + | microcystin | — | Japan | Lyra et al. (2001) |
| Microcystis wesenbergii | NIES 107 | + | microcystin | — | Japan | Lyra et al. (2001) |
| Microcystis aeruginosa | HUB53 | − | — | — | Germany | Lyra et al. (2001) |
| Microcystis aeruginosa | UWOCC C1 | − | — | — | United States | Dempsey (1977) |
| Microcystis aeruginosa | UWOCC C4 | − | — | — | United States | Dempsey (1977) |
| Microcystis aeruginosa | UWOCC P3 | − | — | — | United States | Doers and Parker (1988) |
| Microcystis sp. | UWOCC Bauld B | − | — | — | Australia | Starr and Zeikus (1993) |
| Synechocystis sp. | PCC6803 | − | — | — | United States | Rippka and Herdman (1992) |
| Nostocales | | | | | | |
| Anabaena sp. | strain 202A2 | + | microcystin | — | Finland | Lyra et al. (2001) |
| Anabaena circinalis | NIES 19 | − | — | saxitoxin | England | Neilan et al. (1999) |
| Cylindrospermopsis sp. | strain T3 | − | — | cylindropermopsis | Australia | Hawkins et al. (1997) |
| Nodularia harveyana | PCC7804 | + | nodularin | — | France | Rippka and Herdman (1992) |
| Nodularia harveyana | PCC73104 | − | — | — | Canada | Rippka and Herdman (1992) |
| Nodularia spumigena | NROS 10 | + | nodularia | — | Finland | Bolch et al. (1999) |
| Nodularia spumigena. | BY1 | + | nodularia | — | Baltic Sea | Lehtimaki et al. (1994) |
| Nodularia spumigena. | HEM | + | nodularia | — | Baltic Sea | Lehtimaki et al. (1994) |
| Nostoc sp. | strain 152 | + | microcystin | — | Japan | Lyra et al. (2001) |
| Nostoc sp. | PCC7120 | − | — | — | United States | Lyra et al. (2001) |
| Nostoc sp. | PCC73120 | − | — | — | Australia | Rippka and Herdman (1992) |
| Oscillatoriales | | | | | | |
| Lyngbya sp. | BAN 01 | − | — | n/a | Australia | Salmon (unpublished) |
| Oscillatoria sp. | strain 18R | + | microcystin | — | Finland | Neilan et al. (1999) |
| Oscillatoria sp. | strain 195 | + | microcystin | — | Finland | Neilan et al. (1999) |
| Phormidium tenue | — | − | — | n/a | Japan | Suguira (unpublished) |
| Phormidium sp. | isolate 2-26b | + | microcystin | n/a | United States | Izaguirre et al. 2004 |
| Phormidium sp. | isolate 1-6c | + | microcystin | n/a | United States | Izaguirre et al. (2004) |
| Phormidium sp. | isolate 4-19b | + | microcystin | n/a | United States | Izaguirre et al. (2004) |

[1] As confirmed by PCR in the present study using HEPF/HEPR primers

TABLE 2

Origins of bloom samples screened

| Blue-Green Algal Bloom (dominant genus) | Location | Hepatotoxic | Hepatotoxin | Reference |
|---|---|---|---|---|
| Microcystis sp.* | John Oldman Park Lake, Australia | + | microcystin | Neilan (unpublished) |
| Microcystis sp. | Swan River, Australia | + | microcystin | Neilan (unpublished) |
| Planktothrix sp. | Ammersee, Germany | + | microcystin | Ernst et al 2001 |
| Planktothrix sp.* | Lake Spino, Italy | + | microcystin | Viaggiu B. (personal communication) |
| Nodularia sp.* | Lake Alexandria, Australia | + | nodularin | Moffitt & Neilan 2001 |

All bloom samples tested using primer pair HEPF/HEPR. Only those indicated (*) were tested using primer pair HEPF/HEPR2 or HEPF2/HEPR2.

HCl, pH7.4). The mixture was vortex-mixed and incubated at 65° C. for 2 h and the extracts were cooled for 10 min on ice. Cell debris was removed by centrifugation at 12000×g for 10 min. DNA was precipitated by the addition of 1 volume of isopropanol and ⅒ volume of 4 M ammonium acetate for 15 min at 4° C. The precipitated DNA was pelleted by centrifugation at 12000×g for 10 min and washed with 70% ethanol. The extracted DNA was resuspended in 1100 μl of sterile water.

PCR amplification was performed using various combinations of the primers HEPF (5'-TTTGGGGT-TAACTTTTTTGGGCATAGTC-3') (SEQ ID No:1), HEPR (5'-MTTCTTGAGGCTGTAAATCGGGTT-3') (SEQ ID No:2), HEPF2 (5'-AGTATGATCTGCGGTMAGCA-GATTTCT-3') (SEQ ID No:3) and HEPR2 (5'-AAA-CAAACTCGTTTTTCCCATGT-3') (SEQ ID No:4), as outlined above (see FIG. 2).

All PCR reactions were performed using 0.2 unit Taq polymerase (Fischer Biotech, Perth, Australia) in a 20 μl reaction mix containing 2.5 mM MgCl$_2$, 1×Taq-polymerase buffer (Fischer Biotech), 0.2 mM dNTPs (Fischer Biotech), 0.5 pmol of forward and reverse primer. PCR was performed using 1 μl of template DNA at a concentration of approximately 100 ng μl$^{-1}$. Thermal cycling was in a GeneAmp PCR System 2400 thermocycler (Perkin Elmer, Norwalk, Conn.). The annealing temperature used was 52° C. for the HEPF/HEPR primers, 57° C. for HEPF/HEPR2 and 53° C. for HEPF2/HEPR2. An initial denaturation step at 92° C. for 2 min was followed by 35 cycles of 92° C. for 20 sec, 52° C./57° C./53° C. (as appropriate) for 30 sec, and 72° C. for 1 min, with a final extension step at 72° C. for 5 min. PCR products were analyzed on 1% or 2% agarose gels with 1×TAE-buffer. The PCR products were stained with ethidium bromide (1 μg/ml) for 10 min. For photo documentation a Gel-DOC Bio-RAD System with Quantity One 4.1R software (BIO-RAD, USA) was used.

Sequencing was performed using HEPF, HEPR and HEPF2 primers for each amplification product. Automated sequencing was performed using the PRISM Big Dye cycle sequencing system and ABI 3730 Capillary Applied Biosystem (Foster City, Calif.). The identities of the sequenced amplicons were determined using a BLAST search on GenBank.

A fragment of approximately 472 bp was amplified by PCR using the HEPF/HEPR primer set from DNA of all hepatotoxic strains belonging to *Microcystis, Anabaena, Nostoc, Planktothrix, Phormidium*, and *Nodularia*, whereas no PCR product was obtained from any of the non-toxic strains belonging to *Microcystis, Anabaena, Nostoc, Phormidium, Nodularia, Lyngbya, Synechocystis*, and *Cylindrospermopsis* (data not shown). Thus the PCR results are completely consistent with the designation, as toxic or non-toxic, of all of the species listed in Table 1.

All PCR products were sequenced to confirm the identity of the amplified fragments. Sequence analysis of the amplicons revealed that they represented the expected AMT gene fragment from orthologs of either mcyE or ndaF. The HEPF/HEPR PCR also successfully amplified the 472 bp fragment from all hepatotoxic cyanobacterial bloom samples (see FIG. 3). These fragments were also sequenced and compared with the sequence data from the cultured cyanobacteria.

Further, a fragment of approximately 1000 bp was amplified by PCR using the primer-set HEPF/HEPR2 and about 400 bp using the primer-set HEPF2/HEPR2 from DNA of hepatotoxic strains belonging to *Microcystis, Anabaena, Nostoc, Planktothrix, Phormidium*, and *Nodularia*, whereas no PCR product was obtained from of the non-toxic strain *Microcystis* sp. HUB 53 (see Table 3). These two primer pairs also successfully amplified the fragments from the hepatotoxic cyanobacterial bloom samples originating from John Oldman Park Lake, Lake Spino and Lake Alexandria (see. Table 2), consistent with the results obtained using the HEPF/HEPR primer set (data not shown). The PCR products obtained from the strain *M. aeruginosa* PCC7806 using the HEPF/HEPR2 and HEPF2/HEPR2 primer sets were sequenced to confirm the identity of the amplified fragments. Sequence analysis of the amplicons revealed that they represented the expected AMT gene fragment from mcyE (*M. aeruginosa* PCC7806, accession number: AAF00958).

TABLE 3

Cyanobacterial isolates screened using HEPF/HEPR2 and HEPF2/HEPR2

| Species | Strain | Hepatotoxic | HEPF/ HEPR2 | HEPF2/ HEPR2 | Hepatoxin |
|---|---|---|---|---|---|
| Chroococcales | | | | | |
| *Microcystis aeruginosa* | PCC7806 | + | + | + | microcystin |
| *Microcystis aeruginosa* | HUB53 | − | − | − | — |
| Nostocales | | | | | |
| *Anabaena* sp. | strain 202A2 | + | + | + | microcystin |
| *Anabaena* sp. | strain 90 | + | + | + | microcystin |
| *Nodularia spumigena* | NROS 10 | + | + | + | nodularin |
| *Nostoc* sp. | strain 152 | + | + | + | microcystin |
| Oscillatoriales | | | | | |
| *Oscillatoria* sp. | strain 18R | + | + | + | microcystin |
| *Oscillatoria* sp. | strain 195 | + | + | + | microcystin |
| *Phormidium* sp. | isolate 2-26b | + | + | + | microcystin |
| *Phormidium* sp. | isolate 1-6c | + | + | + | microcystin |
| *Phormidium* sp. | isolate 4-19b | + | + | + | microcystin |

Example 2

Evolution of Cyclic Peptide Hepatotoxin Genes

Sequences from the cultures were aligned and phylogenetically analyzed according to their translated amino acid sequences. The glutamate-1-semialdehyde aminotransferase from *Aquifex* sp. (GenBank Accession No. AE000709) was chosen as the outgroup. Sequences obtained from total bloom DNA was also included in the analysis when the sequences were considered high quality such as the samples Swan River (Australia), Lake Alexandria (Australia), Lake John Oldman Park (Australia), and Lake Spino (Italy).

Sequence data was analyzed using the Applied Biosystem Auto-Assembler computer program. The sequences were compared in a multiple alignment using Clustalx(1.8) and the PAM-Dayhoff matrix. Phylogenetic trees were obtained using the Neighbor-Joining methods and confidence levels were calculated via bootstrapping using a resampling number of 1000. Reference sequences were obtained from GenBank (NCBI).

Figure 3:
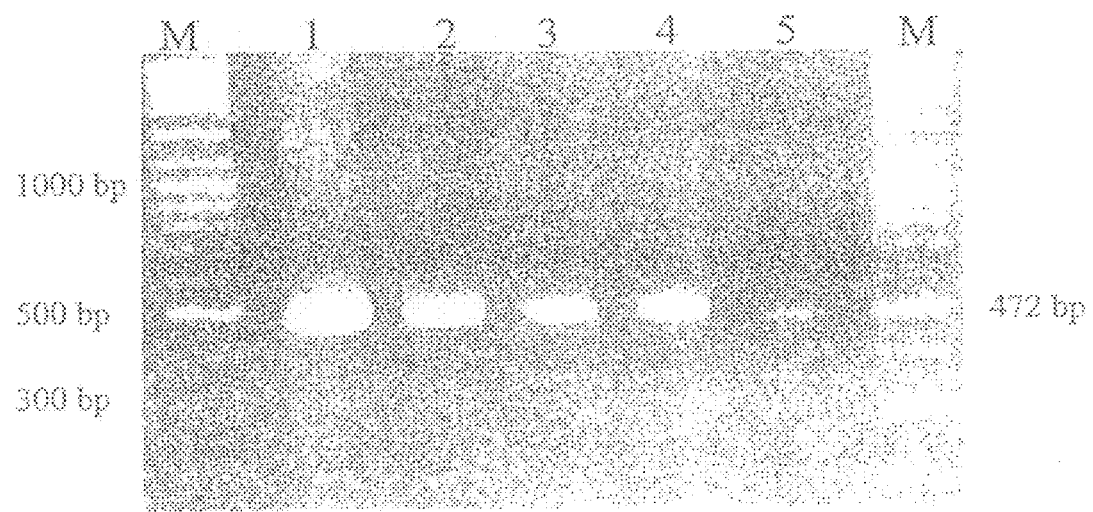
FIG. 3. AMT domain-containing PCR products using HEPF/HEPR primers from blue-green algal bloom samples separated by gel electrophoresis on a 2% agarose gel: M: 1 kb+ DNA-ladder. Lane 1: positive control (*M. aeruginosa* PCC7806), lane 2: Lake Spino (Italy) sample, lane 3: Lake Alexandria (Australia) sample, lane 4: Lake John Oldman Park (Australia) sample, lane 5: Swan River (Australia) sample.

For phylogenetic comparison, the amplified AMT regions from cyanobacterial cultures as well as total bloom material clustered into distinctively different clusters, A and B (FIG. 3). Cluster A comprised strains of the genera *Anabaena*, *Nostoc*, and *Nodularia* belonging to the order Nostocales, while cluster B contained the genera *Oscillatoria/Planktothrix* and *Phormidium*, as well as the hepatotoxic *Microcystis* strains. The sequence data obtained from the *Microcystis* bloom samples grouped with the *Microcystis* strains and the *Nodularia* bloom material aligned with *N. spumigena* NSOR10. Sequence data for the McyE AMT from the different *Oscillatoria/Planktothrix* strains was identical. The same was observed for the three *Phormidium* isolates, however the McyE data for the *Microcystis*, *Anabaena*, and the NdaF sequence data of *Nodularia* strains were not 100% similar.

Figure 4:
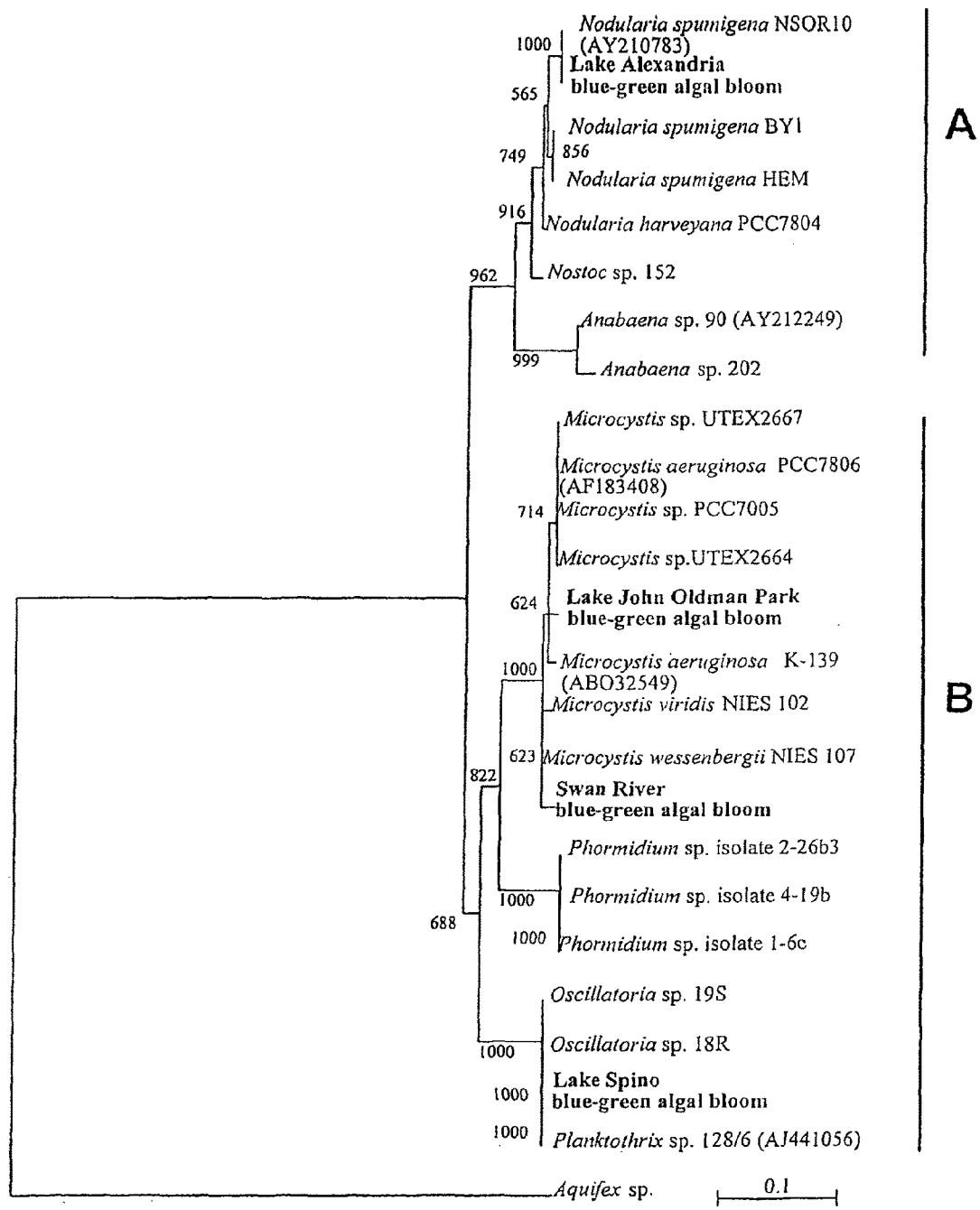
FIG. 4. Phylogenetic analysis of the 472 bp AMT domain-containing PCR fragment. The phylogenetic relationship was constructed using the Neighbor-Joining method. Bootstrap values greater than 500 (after 1000 data resampling events) are shown. The scale is 0.05 mutations per amino acid position. Bloom samples are indicated in bold.

Phylogenetic analysis indicated that NdaF evolved from McyE. Further, the AMT of the nodularin synthetase showed the closest relationship to the AMT from heterocyst-forming microcystin producers and was situated as a sub-branch of AMT of the *Nostoc* strain 152 (FIG. 4).

The phylogeny of AMT revealed clustering according to the genera of the investigated species and therefore these results support the hypothesis that microcystin and nodularin are ancestral relics that have been lost in non-toxic strains. This would suggest the co-evolution of microcystin synthetase, nodularin synthetase, and 16S rDNA.

References

Bolch, C. J. S. et al. 1999. Genetic, morphological, and toxicological variation among globally distributed strains of *Nodularia* (cyanobacteria). *J. Phycol.* 35:339-355.

Carmichael, W. W. 2001. Health effects of toxin-producing cyanobacteria: The CyanoHABs. *Human and ecological risk assessment* 7:1393-1407.

Christiansen, G., J. et al. 2003. Microcystin biosynthesis in *Planktothrix*: genes, evolution, and manipulation. *J. Bacteriol.* 185:564-572.

Codd, G. A. et al. 1999. Cyanobacterial toxins, exposure routes and human health. *Europ. J. Phycol.* 34:405-415.

Dempsey, L. C. 1977. The isolation and characterization of *Microcystis aeruginosa* Kützing emend. Elenkin 1924 from the Lake Winnebago Pool. M.S. thesis. University of Wisconsin, Oshkosh.

Doers, E. P., and D. L. Parker. 1988. Properties of *Microcystis aeruginosa* and *M. flosaquae* (Cyanophyta) in culture: taxonomic implications. *J. Phycol.* 24:502-508.

Eloff, J. N., and A. J. Van der Westhuizen. 1981. Toxicological studies on *Microcystis*, p. 343-364. In W. W. Carmichael (ed.), The Water Environment—Algal Toxins and Health. Plenum. Press, New York.

Ernst et al. 2001. Presence of *Planktothrix* sp. and cyanobacterial toxins in Lake Ammersee, Germany and their impact on whitefish (*Corregonus lavaretus* L.). *Environ. Tox.* 16:483-488.

Hawkins, P. R. et al. 1997. Isolation and toxicity of *Cylindrospermopsis raciborskii* from an ornamental lake. *Toxicon* 35:341-346.

Hisbergues, M. et al. 2003. PCR-based identification of microcystin-producing genotypes of different cyanobacterial genera. *Arch. Microbiol.* 180:402-410.

Hitzfeld, B. et al. 2000. Cyanobacterial toxins: Removal during drinking water treatment, and risk assessment. *Environ. Health Perspect.* 108:113-122.

Izaguirre, G. et al. 2004. A benthic *Phormidium* species that produces microcystin-LR, isolated from three reservoirs in Southern California. 6th International Conference on Toxic Cyanobacteria.

Kurmayer, R. et al. 2004. Abundance of active and inactive microcystin genotypes in populations of the toxic cyanobacterium *Planktothrix* spp. *Environ. Microbiol.* 6:831-841.

Kurmayer, R., and T. Krutzenberger. 2003. Application of real-time PCR for quantification of microcystin genotypes in a population of the toxic cyanobacterium *Microcystis* sp. *Appl. Environ. Microbiol.* 69:6723-6730.

Lehtimäki, J. et al. 1994. The effects of incubation time, temperature, light, salinity, and phosphorus on growth and hepatotoxin production by *Nodularia* strains. *Arch, Hydrobiol.* 130:269-282.

Lyra, C. et al. 2001. Molecular characterization of planktonic cyanobacteria of *Anabaena*, *Aphanizomenon*, *Microcystis* and *Planktothrix* genera. *Int. J. Syst. Evol. Microbiol.* 51:513-526.

Mikalsen, B. et al. 2003. Natural variation in the microcystin synthetase operon mcyABC and impact on microcystin production in *Microcystis* strains. *J. Bacteriol.* 185:2774-2785.

Moffitt, C. M., and B. A. Neilan 2004. Characterization of the nodularin synthetase gene cluster and proposed evolution of cyanobacterial hepatotoxins. *Appl. Environ. Microbiol.* 70:6353-6362.

Moffitt, M. C., and B. A. Neilan 2001. On the presence of peptide synthetase and polyketide synthetase genes in the cyanobacterial genus *Nodularia*. *FEMS Microbiol. Lett.* 196:207-214.

Neilan, B. A. 1995. Identification and phylogenetic analysis of toxigenic cyanobacteria by multiplex randomly amplified polymorphic DNA PCR. *Appl. Environ. Microbiol.* 61:2286-2291.

Neilan, B. A. et al. 1999. Nonribosomal peptide synthesis and toxigenicity of cyanobacteria. *J. Bacteriol.* 181:4089-97.

Neilan, B. A. et al. 2002. Molecular identification of cyanobacteria associated with stromatolites from distinct geographical locations. *Astrobiol.* 2:271-280.

Nishizawa, T. et al. 1999. Genetic analysis of the peptide synthetase genes for a cyclic heptapeptide microcystin in *Microcystis* spp. *J. Biochem.* 126:520-529.

Rippka, R., and M. Herdman. 1992. Pasteur Culture Collection (PCC) of cyanobacterial strains in axenic culture, vol. 1, catalogue of strains. Paris, France; Institut Pasteur.

Rouhiainen, L. et al. 2004. Genes coding for hepatotoxic heptapeptides (microcystins) in the cyanobacterium *Anabaena* strain 90. *Appl. Environ. Microbiol.* 70:686-692.

Starr, R. C., and J. A. Zeikus. 1993. UTEX—the Culture Collection of Algae at The University of Texas at Austin. *J. Phycol.* 29 (Suppl.):1-106.

Tillet, D. et al. 2000. Structural organization of microcystin biosynthesis in Microcystis aeruginosa PCC7806: an integrated peptide-polyketide synthetase system. *Chem. Biol.* 7:753-764.

Vaitomaa, J. et al. 2003. Quantitative real-time PCR for determination of microcystin synthetase E copy numbers for *Microcystis* and *Anabaena* in lakes. *Appl. Environ. Microbiol.* 69:7289-7297.

The claims defining the invention are as follows:

1. A method for determining the absence of microcystin-producing cyanobacteria and nodularin-producing cyanobacteria in a sample, the method comprising analyzing a cyanobacterial sample for the absence of a sequence of a hepatotoxin-associated aminotransferase domain, wherein:
    said sequence is common to the mcyE open reading frame of a microcystin synthetase gene complex and the ndaF open reading frame of a nodularin synthetase gene complex;
    said sequence is located between the polyketide synthase (PKS) and nonribosomal peptide synthetase (NRPS) modules within the mcyE and ndaF open reading frames; and
    said absence of said sequence indicates an absence of microcystin-producing cyanobacteria and nodularin-producing cyanobacteria in said sample; and
    wherein the method comprises using a single primer pair capable of amplifying at least a portion of the hepatotoxin-associated aminotransferase domain from microcystin-producing cyanobacteria and nodularin-producing cyanobacteria.

2. The method of claim 1 wherein the primers are oligonucleotide primers comprising the nucleotide sequences as set forth in SEQ ID Nos: 1 and 2.

3. The method of claim 1 wherein the primers are oligonucleotide primers comprising the nucleotide sequences as set forth in SEQ ID Nos: 1 and 4.

4. The method of claim 1 wherein the primers are oligonucleotide primers comprising the nucleotide sequences as set forth in SEQ ID Nos: 3 and 4.

5. The method of any one of claims 2 to 4 wherein said sample is a sample of salt water or freshwater.

6. The method of any one of claims 2 to 4 wherein said sample is a sample from a blue-green algal bloom.

* * * * *

```
                           SEQUENCE LISTING

<160> NUMBER OF SEQ ID NOS: 9

<210> SEQ ID NO 1
<211> LENGTH: 28
<212> TYPE: DNA
<213> ORGANISM: Artificial Sequence
<220> FEATURE:
<223> OTHER INFORMATION: HEPF oligonucleotide primer sequence

<400> SEQUENCE: 1
tttggggtta acttttttgg gcatagtc                                         28

<210> SEQ ID NO 2
<211> LENGTH: 25
<212> TYPE: DNA
<213> ORGANISM: Artificial Sequence
<220> FEATURE:
<223> OTHER INFORMATION: HEPR oligonucleotide primer sequence

<400> SEQUENCE: 2
aattcttgag gctgtaaatc gggtt                                            25

<210> SEQ ID NO 3
<211> LENGTH: 28
<212> TYPE: DNA
<213> ORGANISM: Artificial Sequence
<220> FEATURE:
<223> OTHER INFORMATION: HEPF2 oligonucleotide primer sequence

<400> SEQUENCE: 3
agtatgatct gcggtaaagc agatttct                                         28

<210> SEQ ID NO 4
<211> LENGTH: 23
<212> TYPE: DNA
<213> ORGANISM: Artificial Sequence
<220> FEATURE:
<223> OTHER INFORMATION: HEPR2 oligonucleotide primer sequence

<400> SEQUENCE: 4
aaacaaactc gttttctccca tgt                                             23

<210> SEQ ID NO 5
<211> LENGTH: 53
<212> TYPE: DNA
<213> ORGANISM: Nodularia spumigena NSOR10

<400> SEQUENCE: 5
tttggggtta acttttttgg tcatagtcaa cccgatttac agcctcaaga att             53

<210> SEQ ID NO 6
<211> LENGTH: 53
<212> TYPE: DNA
<213> ORGANISM: Anabaena sp. 90

<400> SEQUENCE: 6
tttggggtta acttttttgg tcatagtcaa ccagatttac agcctaaaga att             53

<210> SEQ ID NO 7
<211> LENGTH: 53
```

```
<212> TYPE: DNA
<213> ORGANISM: M. aeruginosa PCC7806

<400> SEQUENCE: 7
tttggggtta acttttttgg tcatagtcaa cccgatttac agcctcaaga att            53

<210> SEQ ID NO 8
<211> LENGTH: 53
<212> TYPE: DNA
<213> ORGANISM: M. aeruginosa K-139

<400> SEQUENCE: 8
tttggggtta acttttttgg tcatagtcaa cccgatttac agcctcaaga att            53

<210> SEQ ID NO 9
<211> LENGTH: 53
<212> TYPE: DNA
<213> ORGANISM: Planktothrix sp. 126/8

<400> SEQUENCE: 9
tttggggtta acttttttgg tcatagtcaa cccgatttac aacctcaaga att            53
```